United States Patent
Cheong et al.

(10) Patent No.: US 8,124,199 B2
(45) Date of Patent: Feb. 28, 2012

(54) DISCOTIC LIQUID CRYSTAL COMPOUND, LIQUID CRYSTAL COMPOSITION COMPRISING THE SAME AND OPTICAL FILM USING THE SAME LIQUID CRYSTAL COMPOSITION

(75) Inventors: Jae-Ho Cheong, Daejeon (KR); Min-Jin Ko, Daejeon (KR); Myung-Sun Moon, Daejeon (KR); Bum-Gyu Choi, Daejeon (KR); Dae-Ho Kang, Daejeon (KR); Ki-Youl Lee, Daejeon (KR); Yun-Bong Kim, Seoul (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 12/448,553

(22) PCT Filed: Jan. 22, 2008

(86) PCT No.: PCT/KR2008/000382
§ 371 (c)(1),
(2), (4) Date: Jun. 25, 2009

(87) PCT Pub. No.: WO2008/091088
PCT Pub. Date: Jul. 31, 2008

(65) Prior Publication Data
US 2010/0084608 A1    Apr. 8, 2010

(30) Foreign Application Priority Data

Jan. 22, 2007    (KR) .................. 10-2007-0006582

(51) Int. Cl.
C09K 19/32    (2006.01)
C09K 19/34    (2006.01)
C09K 19/30    (2006.01)
C09K 19/20    (2006.01)
C07F 7/08    (2006.01)

(52) U.S. Cl. .. 428/1.32; 428/1.1; 428/1.33; 252/299.61; 252/299.62; 252/299.63; 252/299.67; 556/438

(58) Field of Classification Search .................. 428/1.1, 428/1.3, 1.32, 1.33; 252/299.01, 299.61, 252/299.62, 299.64, 299.65, 299.66, 299.67; 556/438
See application file for complete search history.

(56) References Cited

U.S. PATENT DOCUMENTS

| | | | |
|---|---|---|---|
| 6,388,146 B1 | 5/2002 | Onishi et al. | |
| 6,630,076 B1 | 10/2003 | Cherkaoui et al. | |
| 2007/0114492 A1* | 5/2007 | Cheong et al. | 252/299.01 |
| 2008/0108727 A1* | 5/2008 | Roberts et al. | 522/172 |
| 2010/0051867 A1* | 3/2010 | Cheong et al. | 252/299.66 |
| 2010/0059712 A1* | 3/2010 | Cheong et al. | 252/299.62 |

FOREIGN PATENT DOCUMENTS

| | | | |
|---|---|---|---|
| JP | 2000-275434 | | 10/2000 |
| JP | 2001002680 A | * | 1/2001 |
| JP | 2003-252880 | | 9/2003 |
| JP | 2005-241710 | | 9/2005 |
| JP | 2006-273781 | | 10/2006 |

OTHER PUBLICATIONS

CAPLUS 2000:749076.*
English translation by computer for JP 2001-2680, http://www4.ipdl. inpit.go.jp/Tokujitu/PAJdetail.ipdl?N0000=60&N0120=01& N2001=2&N3001=2001-002680.*
CAPLUS 2001: 18960.*

* cited by examiner

Primary Examiner — Shean Wu
(74) Attorney, Agent, or Firm — McKenna Long & Aldridge LLP

(57) ABSTRACT

Disclosed is a discotic liquid crystal compound, a liquid crystal composition comprising the same, and an optical film using the same liquid crystal composition. More particularly, there is provided a liquid crystal material of a viewing angle compensation film with high quality characteristics, which can improve a contrast ratio and minimize variations in color with viewing angles in a black state, a liquid crystal composition comprising the same liquid crystal material, and a compensation film obtained from the same liquid crystal composition.

13 Claims, 1 Drawing Sheet

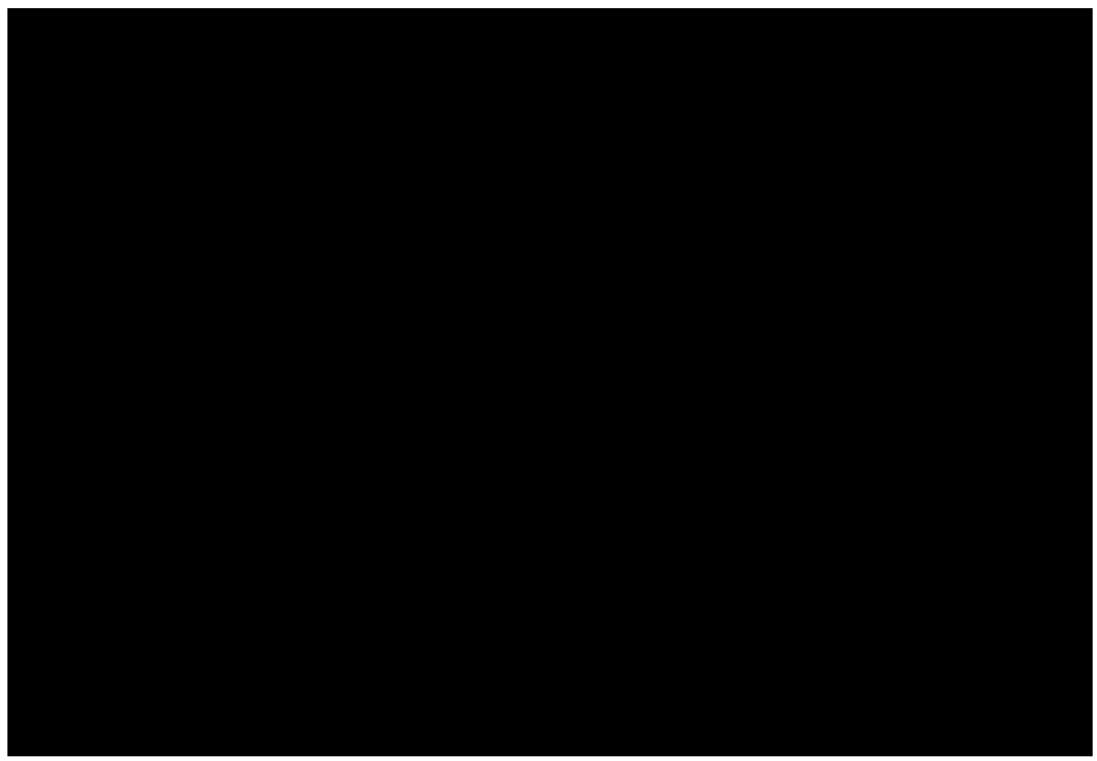

DISCOTIC LIQUID CRYSTAL COMPOUND, LIQUID CRYSTAL COMPOSITION COMPRISING THE SAME AND OPTICAL FILM USING THE SAME LIQUID CRYSTAL COMPOSITION

This application claims the benefit of PCT/KR2008/000382 filed on Jan. 22, 2008, and Korean Application No. 10-2007-0006582 filed on Jan. 22, 2007, the contents of which are hereby incorporated herein by reference for all purposes in their entirety.

TECHNICAL FIELD

The present invention relates to a discotic liquid crystal compound a liquid crystal composition comprising the same, and an optical film using the same liquid crystal composition.

BACKGROUND ART

Recently, as markets on watches, notebook PCs, cellular phones, televisions and monitors have been tremendously extended, the demand for displays of low weight and low power consumption has been greatly increased. A liquid crystal display (LCD), which is light and thin and requires low power consumption, has been widely applied to such products.

However, an LCD has a disadvantage of viewing angle dependency. In other words, an LCD shows variations in color or light/darkness depending on viewing directions or angles. Also, as a size of such an LCD increase, a viewing angle decreases. As compared to a conventional CRT (cathode ray tube) device having a viewing angle of about 180° a TFT-LCD with no viewing angle compensation shows a viewing angle of merely about ±50°.

In order to solve the above described problems, various methods have been used such methods including a multi-domain method in which pixels are divided in liquid crystal cells to control liquid crystal alignment, a method of controlling voltage, and a method of utilizing an optical compensation film.

The above-mentioned viewing angle dependency of an LCD is caused by the incident light having a tilt angle to an LCD panel, which shows a birefringence effect different from that of the vertical incident light. In order to compensate for this, a method of using an optical compensation film has been widely used in which retardation films having opposite birefringence indexes to a panel are attached onto both surfaces of the panel. Also, as the size of a display panel has increased a high-quality liquid crystal compensation film has been needed.

A retardation film is obtained by coating an aligned transparent support with liquid crystal, and aligning the liquid crystal along a predetermined direction to the direction of an aligning layer, followed by curing. After aligning, the liquid crystal has a direction opposite to the direction of liquid crystal cells upon application of voltage, so that light leakage in a black state can be minimized. When such retardation films are combined with a liquid crystal panel so that light is allowed to penetrate through the panel, it is possible to compensate for a light phase difference caused by a difference of light paths because paths of the incident light are similar to each other in all directions. In addition, it is also possible to perform compensation of a difference in birefringence indexes in upper/lower/left/right directions by optimizing the magnitude of birefringence of each film, an angle formed between films, a rubbing direction and an angle to a polarizer.

Therefore, there is a need for a new liquid crystal compound used for manufacturing a viewing angle compensation film having high-quality characteristics of improving a contrast ratio, and minimizing color variations in a black state depending on viewing angles.

DISCLOSURE OF INVENTION

Technical Problem

Therefore, the present invention has been male in view of the above-mentioned problems, and the present invention provides a new discotic liquid crystal compound used for manufacturing a viewing angle compensation film having characteristics of improving a contrast ratio, and minimizing color variations in a black state depending on viewing angles.

Also, the present invention provides a liquid crystal composition comprising such a compound, and an optical film using the same.

Technical Solution

In accordance with an aspect of the present invention, there is provided a new discotic liquid crystal compound, a liquid crystal composition comprising the same, an optical film using the same liquid crystal composition, and a liquid crystal display including the optical film.

A new discotic liquid crystal compound according to the present invention is represented by Formula 1:

[Formula 1]

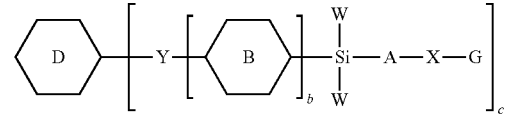

wherein G represents H,

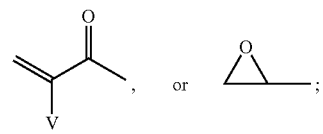

V represents —H, —$CH_3$, —$CH_2CH_3$, —F, —Cl, —Br, or —$CF_3$;

X represents —O—, —NH—, $C_1$~$C_{12}$ alkylene, or a single bond;

A represents $C_1$~$C_{12}$ alkylene, $C_2$~$C_{12}$alkenylene, —$(CH_2CH_2O)_n$—, —$(CH_2CHCH_3O)_n$—, or —$(CHCH_3CH_2O)_n$—, and n represents an integer between 1 and 5;

W represents —H, —$CH_3$, —$CH_2CH_3$, or —$C_6H_5$;

Y represents —O—, —NR—, $C_1$~$C_{18}$ alkylene, —CH=CH—, —C≡C—, —$(CH_2)_oC$(=O)O$(CH_2)_p$—, —$(CH_2)_oOC$(=O)$(CH_2)_p$—, —$(CH_2)_oC$(=O)$(CH_2)_p$—, —$(CH_2)_oC$(=O)NR$(CH_2)_p$—, —$(CH_2)_o$NRC(=O)$(CH_2)_p$—, a single bond, —$SiH_2$—, —$SiMe_2$-, —$SiEt_2$-, —$CH_2SiH_2$—, —$CH_2SiMe_2$-, —$CH_2SiEt_2$-, —$SiH_2CH_2$—, —$SiMe_2CH_2$—, or —$SiEt_2CH_2$—;

each of o and p independently represents an integer between 0 and 2;

R represents H, $C_1$~$C_{20}$ alkyl, $C_2$~$C_{20}$ alkenyl, or $C_2$~$C_{20}$ alkynyl;

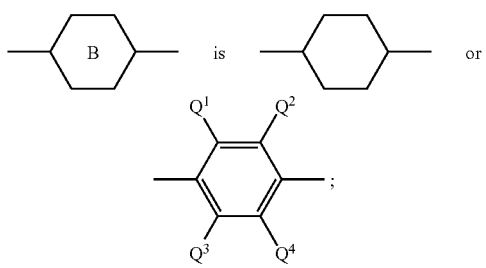

each of $Q^1$~$Q^4$ independently represents —H, —F, —Cl, —Br, —I, —CN, —OH, —$CF_3$, —$CH_3$, —$CH_2CH_3$, —$OCH_3$, —$OCH_2CH_3$, or —C(=O)$CH_3$;

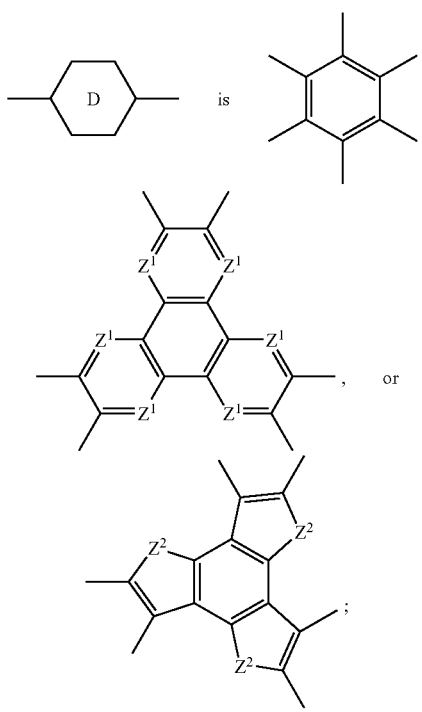

$Z^1$ represents C or N; $Z^2$ represents C, N, O, or S;
b represents an integer between 0 and 2; and
c represents an integer between 1 and 6.

BRIEF DESCRIPTION OF THE DRAWINGS

The foregoing and other objects, features and advantages of the present invention will become more apparent from the following detailed description when taken in conjunction with the accompanying drawing in which:

FIG. 1 is a photograph taken by a polarizing microscope in a black state when a compensation film manufactured according to Example 3 of the present invention is used.

BEST MODE FOR CARRYING OUT THE INVENTION

A compound represented by Formula 1 of the present invention is a polymerizable liquid crystal compound.

Specifically, in a discotic liquid crystal compound according to the present invention, a polymerizable group as a substituent is introduced to a disc-shaped core. However, when a polymerizable group is directly attached to a disc-shaped core, it is difficult to maintain an alignment state in polymerization. Therefore, a linking group is introduced between the disc-shaped core and the polymerizable group.

In Formula 1, ring D or ring D-(Y-ring B), represents a ring-shaped core, G represents a polymerizable group, and Si-A-X represents a linking group.

The compound represented by Formula 1, which is a discotic liquid crystal compound, has high stacking ability, and accordingly, can be used for a TN mode compensation film or O-plate (splay) type compensation film.

Also, in the compound represented by Formula 1, Si is introduced, thereby improving the processibility of a liquid crystal compound.

The compound represented by Formula 1 of the present invention is easily mixed with various liquid crystal materials, and has high solubility even at low temperatures. Also, the compound represented by Formula 1 is physically and chemically stable and is stable against heat and light, under the application conditions of conventional liquid crystal displays, and forms a liquid crystal mesophase at a preferred range of temperatures. Therefore, the compound represented by Formula 1 may be very useful for forming a liquid crystal composition. In addition, contrary to a conventional liquid crystal composition which is deposited as a crystal at room temperature, there is no deposition in a liquid crystal composition comprising the compound represented by Formula 1 of the present invention, even when the composition is stored at room temperature for longer than a week.

Therefore, the compound represented by Formula 1 is a liquid crystal compound applicable to an optical film which improves a wide viewing angle of various liquid crystal displays.

In Formula 1, $C_2$~$C_{12}$ alkenylene as A is selected from the group including —CH=CH—, —CH=CCH$_3$—, —CH$_2$CH=CH—, —CH=CHCH$_2$CH$_2$—, —CH$_2$CH=CHCH$_2$—, —CH$_2$CH$_2$CH=CH—, —CH=CHCH$_2$CH$_2$CH$_2$—, —CH$_2$CH=CHCH$_2$CH$_2$—, —CH$_2$CH$_2$CH=CHCH$_2$—, and —CH$_2$CH$_2$CH$_2$CH=CH—.

Hereinafter, a method of preparing the compound represented by Formula 1 will be explained, but the scope of the present invention is not limited thereto.

The compound represented by Formula 1 may be prepared by Reaction Scheme 1.

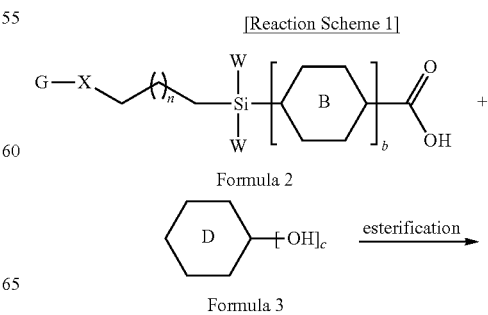

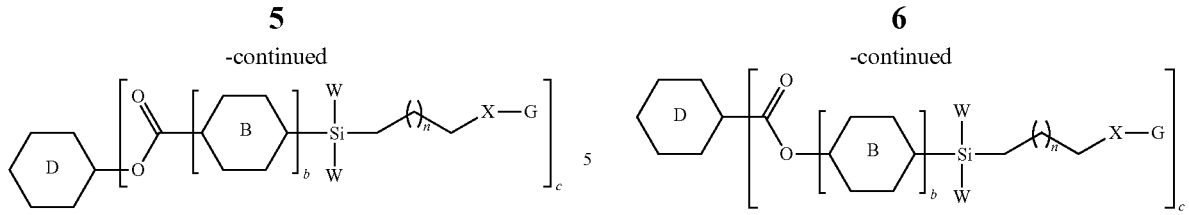

Also, the compound represented by Formula 1 may be prepared by Reaction Scheme 2.

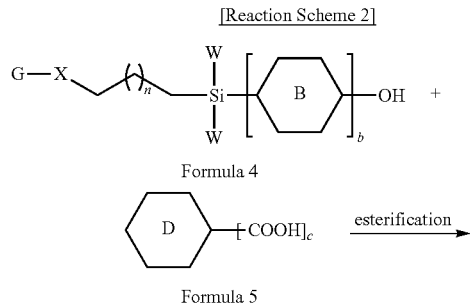

In Reaction Schemes 1 and 2, G, X, W, ring B, ring D, b, and c are the same as defined in Formula 1, and n represents an integer between 1 and 10.

The discotic liquid crystal compound according to the present invention may be obtained through esterification of the compounds represented by Formulas 2 and 3 in Reaction Scheme 1. Also, the discotic liquid crystal compound according to the present invention may be obtained through esterification of the compounds represented by Formulas 4 and 5 in Reaction Scheme 2. As a reagent in the esterification, DCC (dicyclohexylcarbodiimide), EDC(1-ethyl-3-(3-dimethylamino)propyl)carbodiimide), $SOCl_2$, $COCl_2$, or MsCl(m-esyl chloride), etc. may be used and other conventional reagents known in the art also may be used.

Herein, the compound represented by Formula 2 in Reaction Scheme 1 may be prepared by Reaction Scheme 3, and the compound represented by Formula 4 in Reaction Scheme 2 may be prepared by Reaction Scheme 4

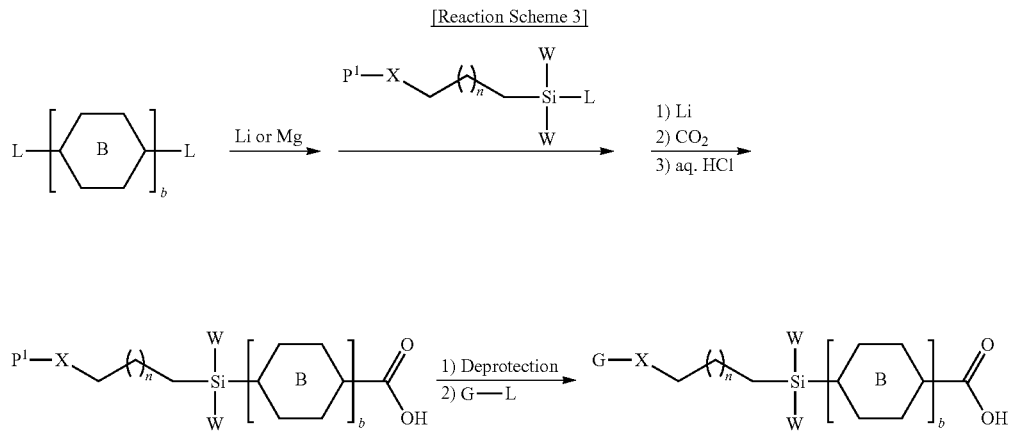

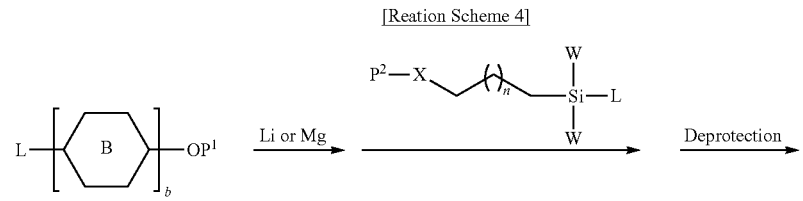

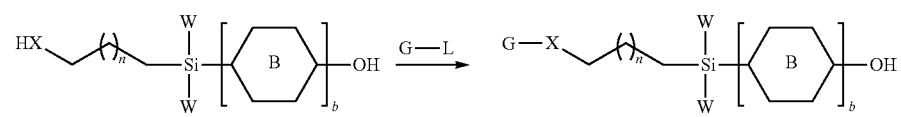

In Reaction Schemes 3 and 4, L represents a leaving group, and non-limiting examples of the leaving group include, but are not limited to, halide, mesylate($-OSO_2CH_3$), tosylate($-OSO_2C_6H_5$-p-$CH_3$), etc. Also, each of $P^1$ and $P^2$ independently represents a protecting group such as THP(tetrahydropyranyl), TBS(t-butyldimethylsilyl), etc., but other conventional protecting groups known in the art also may be included. G, X, W, ring B, and b are the same as defined in Formula 1, and n represents an integer between 1 and 10.

In lithiation using Li in Reaction Schemes 3 and 4, instead of Li, other reagents (for, example BuLi), which are appropriate for the lithiation, may also be used without any particular limitation. Also, in the step of deprotection, conventional reagents known in the art may be used.

Also, silicon derivative, which is added as a reactant in the second steps of Reaction Schemes 3 and 4, may be prepared by Reaction Scheme 5.

[Reaction Scheme 5]

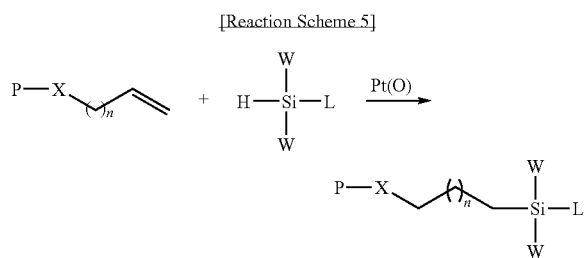

In Reaction Scheme 5, if X is —O—, or —NH—, P is $P^1$ or $P^2$, and also, if X is $C_1$~$C_{12}$ alkylene or a single bond, P is L. Herein, $P^1$, $P^2$, and L are the same as defined in Reaction Schemes 3 and 4

A method for preparing the compound represented by Formula 1 also includes other methods performed via a reaction path similar to Reaction Schemes 1-5.

The present invention provides a liquid crystal composition comprising the compound represented by Formula 1.

The compound represented by Formula 1 is included in the liquid crystal composition in an amount of 0.1~99.9 wt %, preferably of 1~80 wt %, based on the total weight of the composition.

In addition to the above liquid crystal compound represented by Formula 1, the liquid crystal composition according to the present invention may include other various compounds, which can be mixed without disturbing liquid crystal properties. Examples of such compounds include a polymerizable liquid crystal compound a polymerizable non-liquid crystal compound and a polymer, which are currently used in a conventional liquid crystal composition, and may be used at various ratios as desired. It is preferable that each of the polymerizable compounds has a polymerizable group, such as a vinyl group, a vinyloxy group, an acrylic group, or a methacrylic group.

The liquid crystal composition according to the present invention may include a photoreaction initiator as required and herein, the photoreaction initiator may include conventional initiators known in the art without any particular limitation. Non-limiting examples of the photoreaction initiator include benzoyl ether, benzoyl isobutyl ether, benzoyl isopropyl ether, benzophenone, acetophenone, 4-benzoyl-4'-methyl diphenyl sulfide, benzyl methyl ketal, dimethylamino methyl benzoate, 3,3'-dimethyl-4-methoxybenzophenone, methyl benzoylformate, 2-methyl-1-(4-methylthio)phenyl)-2-morpholinopropane-1-one, 2-benzyl-2-dimethylamino-1-(4-morpholinophenyl)-butane-1-one, 1-hydroxycyclohexyl phenyl ketone, Irgacure based etc. Also, the photoreaction initiator may be aided in an amount of 0.001 to 20 parts by weight, preferably 0.01 to 10 parts by weight, based on 100 parts by weight of a polymerizable liquid crystal compound.

Also, the liquid crystal composition according to the present invention may include an organic solvent as required. The inclusion of the organic solvent facilitates the application (coating) of the liquid crystal composition on a substrate such as a film.

Herein, as the organic solvent, conventional organic solvents known in the art may be used without any particular limitation. Non-limiting examples of the organic solvent include: hydrocarbons such as cyclohexane, cyclopentane, benzene, toluene, xylene, butylbenzene, etc.; ketones such as acetone, methyl ethyl ketone, methyl isobutyl ketone, cyclohexanone, etc.; esters such as ethyl acetate, ethylene glycol monomethyl ether acetate, propylene glycol monomethyl ether acetate, gamma-butyrolactone, etc.; amides such as 2-pyrrolidone, N-methyl-2-pyrrolidone, dimethyl formamide, dimethylacetamide, etc.; halogens such as chloroform, dichloromethane, carbon tetrachloride, dichloroethane, tetrachloroethane, tetrachloroethylene, chlorobenzene, etc.; alcohols such as t-butyl alcohol, diacetone alcohol, glycerin, monoacetin, ethylene glycol, triethylene glycol, hexylene glycol, ethylene glycol monomethyl ether, etc.; phenols such as phenol, parachlorophenol, etc.; and ethers such as methoxybenzene, 1,2-dimethoxybenzene, diethylene glycol dimethyl ether, ethylene glycol dimethyl ether, ethylene glycol diethyl ether, propylene glycol dimethyl ether, propylene glycol diethyl ether, diethylene glycol dimethyl ether, diethylene glycol diethyl ether, dipropylene glycol dimethyl ether, dipropylene glycol diethyl ether, etc. Also, such an organic solvent can be independently used, or can be used by mixing at least two of these materials, and herein, the usage amount is not limited.

Also, the liquid crystal composition according to the present invention may include a surfactant as required. A surfactant allows a liquid crystal composition to be easily applied on a substrate. As the surfactant, conventional surfactants known in the art may be used without any particular limitation, and the additional amount varies according to the kind of surfactant, the composition ratio of components of a liquid crystal composition, the kind of solvent, and the kind of substrate.

Also, the liquid crystal composition according to the present invention may include a chiral dopant or a leveling agent that prevents distortion of a spiral structure of liquid crystal or reverse distortion of liquid crystal, etc. as an additional additive.

The liquid crystal composition according to the present invention may be prepared in a conventional manner. Typically, in the preparation, various components are dissolved at room temperature or high temperature.

The present invention provides an optical film using the liquid crystal composition according to the present invention.

The optical film according to the present invention is manufactured by forming an optically anisotropic layer, that is, a liquid crystal film, on a substrate. Herein, a liquid crystal alignment state in the liquid crystal film can be adjusted by appropriately selecting a polymerizable liquid crystal compound forming a liquid crystal composition, and other compounds.

Non-limiting examples of the optical film according to the present invention include an A-plate type compensation film, a B-plate type compensation film, a (+)C-plate type compensation film, a (−)C-plate type compensation film, or an O-plate(splay) type compensation film, etc.

In the optical film of the present invention, the substrate may be used without any particular limitation, so long as the liquid crystal film can be formed on its surface. Examples of such the substrate include a polymer film, a metal, or a glass, etc.

Non-limiting examples of the polymer film include polyimide, polyamide imide, polyamide, polyetherimide, polyetheretherketone, polyetherketone, polyketone sulfide, polyethersulfone, cycloolefin polymer, polysulfone, polyphenylene sulfide, polyphenylene oxide, polyethylene terephthalate, polybutylene terephthalate, polyethylene naphthalate, polyacetal, polycarbonate, polyacrylate, acrylic resin, polyvinyl alcohol, polypropylene, cellulose, triacetyl cellulose, epoxy resin, phenol resin, etc., and herein the examples may be a uniaxially oriented film or a biaxially oriented film. Also the polymer film may be used after surface treatment such as hydrophilic treatment or hydrophobic treatment, and may be a laminated film. Also, non-limiting examples of the metal include aluminum, iron, copper, etc., which have slit-shaped surface grooves; and non-limiting examples of the glass include alkali glass, boric glass, print glass, etc., which have slit-shaped surfaces through etching.

Also, the substrate may have an alignment layer thereon. Non-limiting examples of a material for the alignment layer include polyimide, polyamide, polyacrylate, polyvinyl alcohol, etc.

Some of the substrate materials can be directly used due to sufficient capability of aligning a liquid crystal compound. However, in order to enhance alignment capability, the substrate materials may be subjected to separate treatment, such as rubbing, stretching, polarization irradiation, or skew ray irradiation, before being used as the substrate.

Herein, the rubbing can be directly performed on a substrate, or can be performed on an alignment layer previously formed on a substrate.

The optical film according to the present invention may be fabricated by common methods well known in the art. As an example, the optical film of the present invention may be fabricated by coating the inventive liquid crystal composition on a substrate, drying the coated liquid crystal composition to thereby aligning the liquid crystal compound, and then curing the aligned liquid crystal compound while maintaining the alignment form of the liquid crystal compound to thereby fix the alignment form.

The coating of a liquid crystal composition on a substrate may be performed in a conventional manner. Non-limiting examples of such a coating include spin coating, roll coating, printing, dip-drawing coating, curtain coating, die coating, dip coating, etc.

The drying process may be performed in a conventional manner, and herein, a liquid crystal compound is aligned during the drying process or is aligned by additionally heating after the drying process. The conditions of drying vary according to a boiling point of an organic solvent used for a liquid crystal composition, and materials for a substrate and an alignment layer, without any particular limitation. Also, it is possible to dry by heating, or to gradually dry at room or low temperature.

The curing process may be performed by irradiating rays and/or heat-treating on a coated liquid crystal composition. In the process, polymerization is carried out by a polymerizable group of a polymerizable compound and a liquid crystal compound with a fixed alignment is attached on a substrate, thereby forming a liquid crystal film with an optically anisotropic layer. The wavelengths of the rays used for the curing process may include, but are not limited to, electron beams, ultraviolet rays, visible rays, infrared rays, etc. Also, the heat-treating is generally performed at 10~200° C. from 3 seconds to 30 minutes, but the conditions of the heat-treating are not limited to this.

Also, the optical film according to the present invention may be manufactured by coating a liquid crystal composition on a peelable film, drying the composition, forming a liquid crystal film through a curing process, and transferring the formed liquid crystal film to a substrate by using a gluing agent or adhesives.

The optical film according to the present invention may be used as an optical compensation film or a polarizer using the optical compensation film, and may be provided in a liquid crystal display.

Reference will now be male in detail to the preferred embodiments of the present invention. However, the following examples are illustrative only, and the scope of the present invention is not limited thereto.

EXAMPLE 1

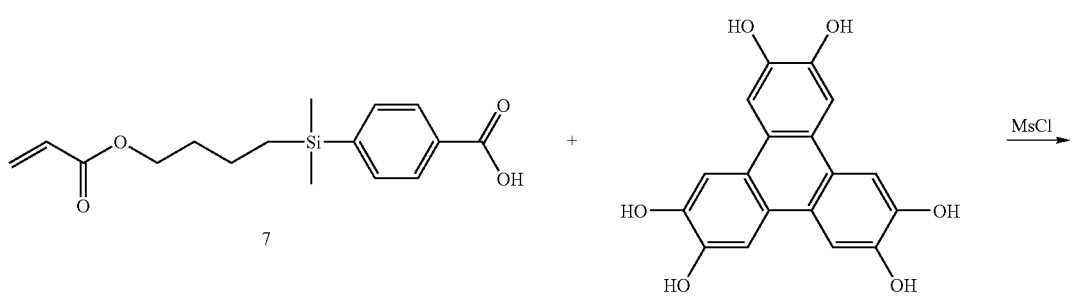

-continued

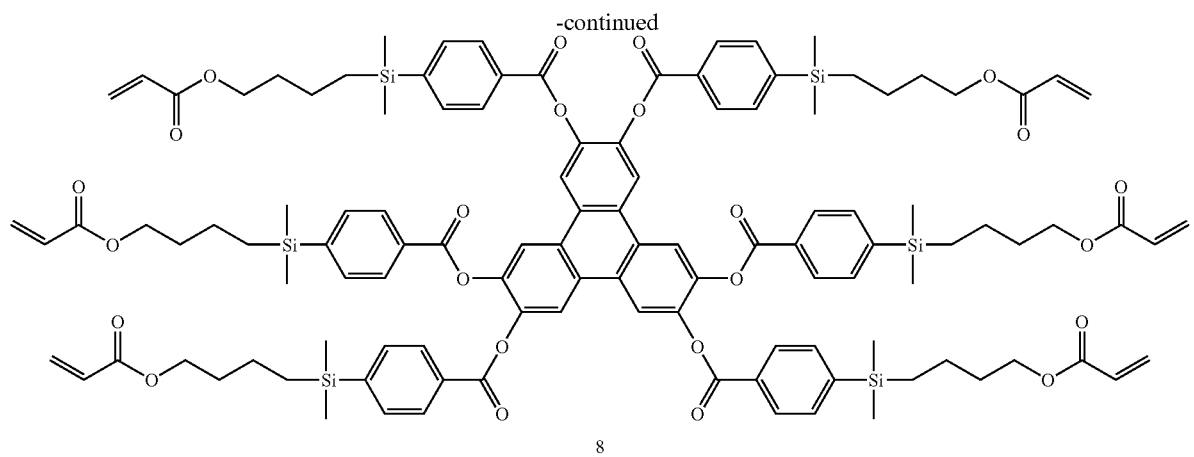

8

1.0 equivalent of a compound 7 was dissolved in a dry THF solvent and a $CH_2Cl_2$ solvent, and 1 equivalent of MsCl and 1.1 equivalents of N,N-diisopropylethyl amine were added at 0° C., and then, acid chloride was prepared through stirring for 30 minutes. Next, 1.1 equivalents of N,N-diisopropylethylamine, 0.3 equivalents of DMAP, and 0.1 equivalents of 2,3,6,7,10,11-hexahydroxytriphenylene were added to acid chlorite at 0° C. Then, after stirring at room temperature under a nitrogen atmosphere for about 20 hours, the mixture was worked up with water and ether and separated via silica gel column chromatography to obtain a compound 8 at a yield of about 80%. $^1$HNMR (400 MHz, $CDCl_3$): δ 0.29 (s, 36H), 0.66~0.78 (m, 12H), 1.55~1.78 (m, 12H), 1.80~1.93 (m, 12H), 4.13 (t, 12H), 5.82 (d, 6H), 6.12 (dd, 6H), 6.40 (d, 6H), 7.15 (d, 12H), 7.89 (d, 12H), 8.37 (s, 6H).

EXAMPLE 2

(d, 6H), 6.12 (dd, 6H), 6.41 (d, 6H), 7.15 (d, 12H), 7.89 (d, 12H), 8.43 (s, 6H).

EXAMPLE 3

Manufacture of a Liquid Crystal Composition and a Compensation Film

First, 9.28 g of the liquid crystal compound 8 according to Example 1 was dissolved in 30 g of methyl ethyl ketone. Next, 600 mg of Irgacure 907 (2-Methyl-4'-(methylthio)-2-morpholinophenone), 40 mg of FC-4430 as alignment promoter, and 80 mg of BYK-300 as leveler were ached thereto, and the reaction mixture was sufficiently shaken. After complete dissolution, particles were removed using a particle filter, thereby preparing coating liquid (a liquid crystal composition). Then, a rubbing process was performed on a glass with

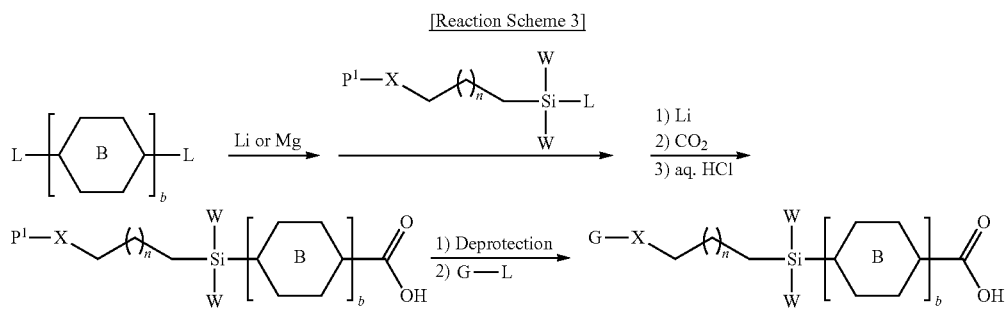

[Reaction Scheme 3]

1.0 equivalent of a compound 9 was dissolved in a dry THF solvent and a $CH_2Cl_2$ solvent, and 1 equivalent of MsCl and 1.1 equivalents of N,N-diisopropylethyl amine were added at 0° C., and then, acid chlorite was prepared through stirring for 30 minutes. Next, 1.1 equivalents of N,N-diisopropylethylamine, 0.3 equivalents of DMAP, and 0.1 equivalents of 2,3,6,7,10,11-hexahydroxytriphenylene were ailed to acid chlorite at 0° C. Then, after stirring at room temperature under a nitrogen atmosphere for about 20 hours, the mixture was worked up with water and ether and separated via silica gel column chromatography to obtain a compound 10 at a yield of about 82%. $^1$HNMR (400 MHz, $CDCl_3$): δ 0.30 (s, 36H), 0.67~0.80 (m, 12H), 1.59~1.83 (m, 12H), 4.14 (t, 12H), 5.83 a PVA alignment layer, and the prepared coating liquid was spin-coated on the glass at 2000 rpm for 20 seconds. The coated product was dried in an oven at 150° C. for 1 minute, and UV rays (200 W-80 W/m) were irradiated thereto to provide a compensation film.

EXAMPLE 4

Manufacture of a Liquid Crystal Composition and a Compensation Film

A compensation film was manufactured in the same manner as described in Example 3, except that the liquid crystal compound 10 according to Example 2 was used instead of the liquid crystal compound 8 according to Example 1.

COMPARATIVE EXAMPLE 1

Manufacture of a Liquid Crystal Composition and a Compensation Film

A compensation film was manufactured in the same manner as described in Example 3, except that a conventional discotic liquid crystal compound (2,3,6,7,10,11-Hexakis(4-(4-acryloxybutane-1-oxy)benzenecarbonyloxy)triphenylene) (Fuji) was used instead of the liquid crystal compound 8 according to Example 1.

[Determination of Physical Properties of a Compensation Films]

For each of the compensation films according to Examples 3 and 4, its thickness, refractive index, retardation, and viewing angle, etc. were measured.

Specifically, the thickness was measured by using a microgauge, and the birefringence index was measured at a center wavelength of 550 nm by using an Abbe refractometer. Also, the value of wavelength dispersion with a ratio of 450 nm/650 nm was obtained by measuring UV dispersion by an Axo scan apparatus, and the viewing angles in upper/lower/left/right directions were measured by attaching each of the compensation films to a TN liquid crystal display. The results are shown in Table 1.

TABLE 1

| Compensation film | Thickness (μm) | Birefringence Index (Δn) | Wavelength dispersion (450 nm/650 nm) | Viewing angles Upper/lower, left/right |
|---|---|---|---|---|
| Ex. 3 | 2 | 0.07 | 1.16 | 95°, 150° |
| Ex. 4 | 2 | 0.07 | 1.17 | 93°, 152° |
| Comp. Ex. 1 | 2 | 0.08 | 1.21 | 75°, 135° |

As can be seen from Table 1, the compensation films obtained by using the discotic liquid crystal compound according to the present invention have wider viewing angles than a conventional film.

FIG. 1 is a photograph taken by a polarizing microscope in a black state when a compensation film according to Example 3 is used.

In general, a compensation film is used to prevent light leakage in a black state. Since the degree of black color in the black state is important in contrast and a viewing angle, it can be said that the purer the black color, the better the compensation film. Therefore, with reference to the pure black state photograph taken by a polarizing microscope shown in FIG. 1, the surface quality and the alignment state of the film according to Example 3 are determined, and accordingly, it is determined that the film has an excellent alignment state, and thus is suitable for an optical compensation film.

Industrial Applicability

As can be seen from the foregoing, a high-quality viewing angle compensation film, which improves a contrast ratio measured at a tilt angle when compared to a contrast ratio measured from the front surface, and minimizes color variations in a black state depending on viewing angles, can be fabricated by using the liquid crystal composition comprising the discotic liquid crystal compound according to the present invention.

Although several exemplary embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A compound represented by Formula 1:

[Formula 1]

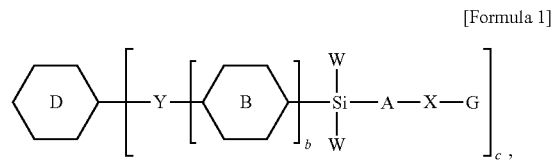

wherein G represents

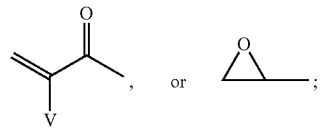

V represents —H, —CH$_3$, —CH$_2$CH$_3$, —F, —Cl, —Br, or —CF$_3$;

X represents —O—, —NH—, C$_1$~C$_{12}$ alkylene, or a single bond;

A represents C$_1$~C$_{12}$ alkylene, C$_2$~C$_{12}$ alkenylene, —(CH$_2$CH$_2$O)$_n$—, —(CH$_2$CHCH$_3$O)$_n$—, or —(CHCH$_3$CH$_2$O)$_n$—, and n represents an integer between 1 and 5;

W represents —H, —CH$_3$, —CH$_2$CH$_3$, or —C$_6$H$_5$;

Y represents —O—, —NR—, C$_1$~C$_{18}$ alkylene, —CH=CH—, —C≡C—, —(CH$_2$)$_o$C(=O)O(CH$_2$)$_p$—, —(CH$_2$)$_o$OC(=O)(CH$_2$)$_p$—, —(CH$_2$)$_o$C(=O)(CH$_2$)$_p$—, —(CH$_2$)$_o$C(=O)NR(CH$_2$)$_p$—, —(CH$_2$)$_o$NRC(=O)(CH$_2$)$_p$—, a single bond, —SiH$_2$—, —SiMe$_2$-, —SiEt$_2$-, —CH$_2$SiH$_2$—, —CH$_2$SiMe$_2$-, —CH$_2$SiEt$_2$-, —SiH$_2$CH$_2$—, —SiMe$_2$CH$_2$—, or —SiEt$_2$CH$_2$—;

each of o and p independently represents an integer between 0 and 2;

R represents H, C$_1$~C$_{20}$ alkyl, C$_2$~C$_{20}$ alkenyl, or C$_2$~C$_{20}$ alkynyl;

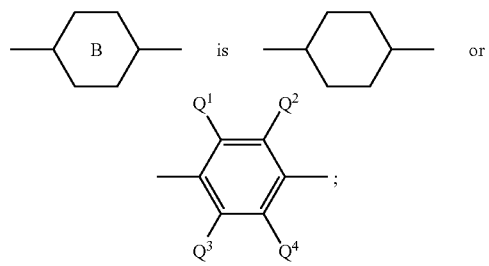

each of Q$^1$~Q$^4$ independently represents —H, —F, —Cl, —Br, —I, —CN, —OH, —CF$_3$, —CH$_3$, —CH$_2$CH$_3$, —OCH$_3$, —OCH$_2$CH$_3$, or —C(=O)CH$_3$;

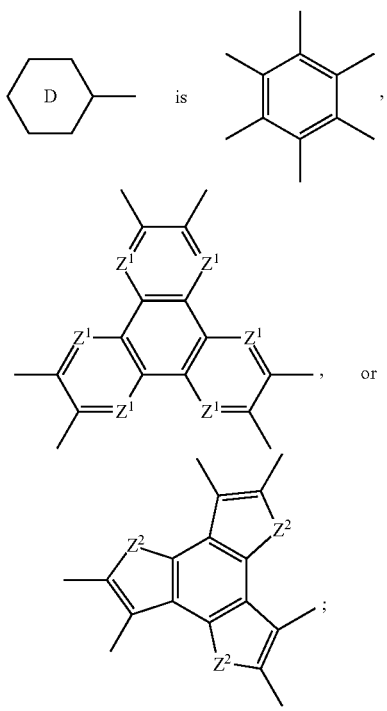 is $Z^1$ represents C or N, $Z^2$ represents C, N, O, or S;
b represents an integer between 0 and 2; and
c represents an integer ranging from 2 to 6.

2. The compound as claimed in claim 1, wherein the $C_2$~$C_{12}$ alkenylene as A is selected from the group including —CH=CH—, —CH=CCH$_3$—, —CH$_2$CH=CH—, —CH=CHCH$_2$CH$_2$—, —CH$_2$CH=CHCH$_2$—, —CH$_2$CH$_2$CH=CH—, —CH=CHCH$_2$CH$_2$CH$_2$—, —CH$_2$CH=CHCH$_2$CH$_2$—, —CH$_2$CH$_2$CH=CHCH$_2$—, and —CH$_2$CH$_2$CH$_2$CH=CH—.

3. The compound as claimed in claim 1, which is a compound prepared by Reaction Scheme 1:

[Reaction Scheme 1]

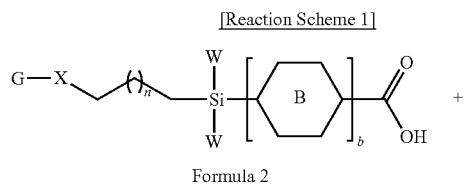

Formula 2

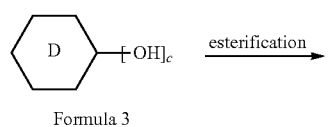

Formula 3

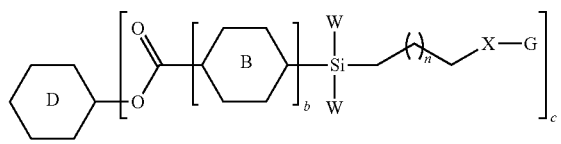

wherein G, X, W, ring B, ring D, b, and c are the same as defined in claim 1, and n represents an integer between 1 and 10.

4. The compound as claimed in claim 3, wherein the compound represented by Formula 2 is prepared by Reaction Scheme 3:

[Reaction Scheme 3]

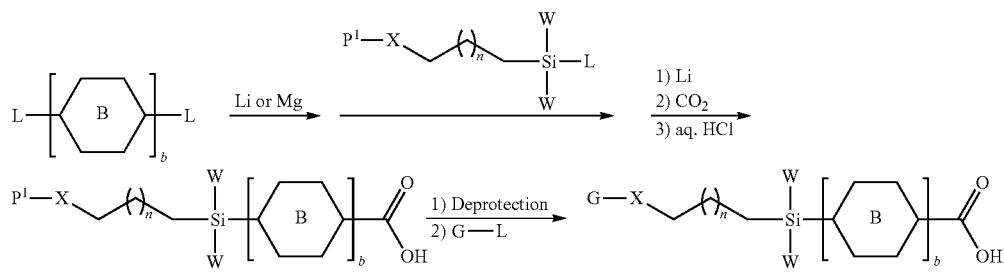

wherein G, X, W, ring B, and b are the same as defined in claim 1, L represents a leaving group, $P^1$ represents a protecting group, and n represents an integer between 1 and 10.

5. The compound as claimed in claim 1, which is a compound prepared by Reaction Scheme 2:

[Reaction Scheme 2]

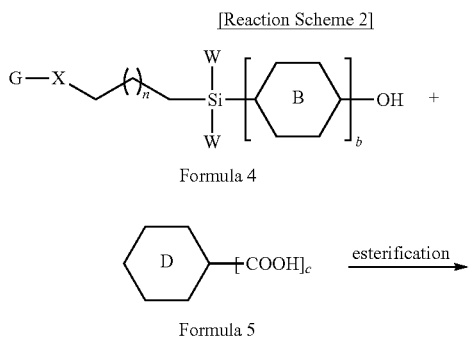

Formula 4

Formula 5

-continued

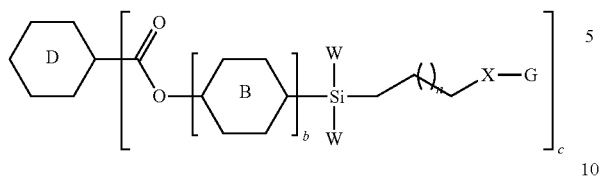

wherein G, X, W, ring B, ring D, b, and c are the same as defined in claim 1, and n represents an integer between 1 and 10.

6. The compound as claimed in claim 5, wherein the compound represented by Formula 4 is prepared by Reaction Scheme 4:

[Reation Scheme 4]

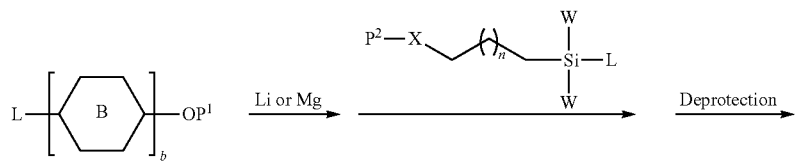

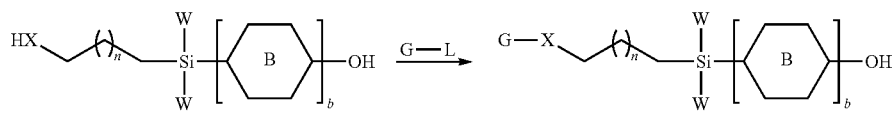

wherein G, X, W, ring B, and b are the same as defined in claim 1, L represents a leaving group, each of $P^1$ and $P^2$ independently represents a protecting group, and n represents an integer between 1 and 10.

7. A liquid crystal composition comprising the compound represented by Formula 1 as claimed in claim 1:

[Formula 1]

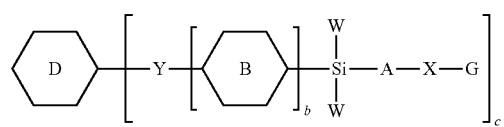

wherein G, X, A, W, Y, ring B, ring D, b and c are the same as defined in claim 1.

8. The liquid crystal composition as claimed in claim 7, wherein the compound represented by Formula 1 is used in an amount of 1~80 wt % based on the total weight of the composition.

9. An optical film using a liquid crystal composition comprising the compound represented by Formula 1 as claimed in claim 1:

[Formula 1]

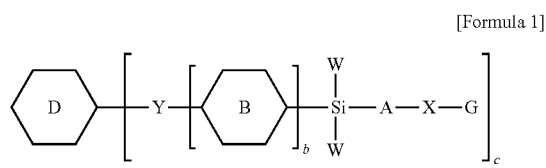

wherein G, X, A, W, Y, ring B, ring D, b and c are the same as defined in claim 1.

10. The optical film as claimed in claim 9, wherein the compound represented by Formula 1 is used in an amount of 1~80 wt % based on the total weight of the composition.

11. The optical film as claimed in claim 9, which is an A-plate type compensation film, a B-plate type compensation film, a (+) C-plate type compensation film, a (−)C-plate type compensation film, or an O-plate (splay) type compensation film.

12. A liquid crystal display comprising the optical film as claimed in claim 9.

13. The liquid crystal display as claimed in claim 12, wherein the compound represented by Formula 1 is used in an amount of 1~80 wt % based on the total weight of the composition.

* * * * *